(12) United States Patent
Kobilka et al.

(10) Patent No.: US 9,822,208 B1
(45) Date of Patent: Nov. 21, 2017

(54) FLAME RETARDANT MATERIALS DERIVED FROM FURAN DICARBOXYLIC METHYL ESTER

(71) Applicant: International Business Machines Corporation, Armonk, NY (US)

(72) Inventors: Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/397,406

(22) Filed: Jan. 3, 2017

(51) Int. Cl.
*C08F 234/02* (2006.01)
*C08L 45/00* (2006.01)
*C08K 5/5373* (2006.01)
*C07F 9/655* (2006.01)
*C08G 63/692* (2006.01)
*C08G 79/04* (2006.01)

(52) U.S. Cl.
CPC ........ *C08F 234/02* (2013.01); *C07F 9/65515* (2013.01); *C08K 5/5373* (2013.01); *C08L 45/00* (2013.01); *C08L 2201/02* (2013.01)

(58) Field of Classification Search
CPC .. C07F 9/65515; C08F 234/02; C08K 5/5373; C08L 2201/02; C08G 63/692; C08G 79/04
USPC .......................................... 528/287; 549/218
See application file for complete search history.

(56) References Cited

U.S. PATENT DOCUMENTS

| 8,680,183 | B2 | 3/2014 | Schambony et al. |
| 8,779,040 | B2 | 7/2014 | van der Weele et al. |
| 8,781,278 | B2 | 7/2014 | Karayianni |
| 8,859,788 | B2 | 10/2014 | Partin et al. |
| 9,145,379 | B2 * | 9/2015 | Graβ ..................... C07D 307/68 |
| 9,238,609 | B2 | 1/2016 | Asthana et al. |
| 9,284,414 | B2 | 3/2016 | Boday et al. |
| 9,309,407 | B2 | 4/2016 | Rosenquist |
| 2012/0252911 | A1 * | 10/2012 | Fleckenstein .......... C08J 9/0038 521/55 |

(Continued)

FOREIGN PATENT DOCUMENTS

| CN | 104262905 A | 1/2015 |
| GB | 2499491 B | 7/2016 |
| WO | WO-2015095466 A2 | 6/2015 |

OTHER PUBLICATIONS 2,5-Furanedicarbonyl dichloride: Structure, Names and Synonyms, ChemSpider (http://www.chemspider.com/Chemical-Structure.9655788.html), Royal Society of Chemistry 2015 (3 pages).*

(Continued)

*Primary Examiner* — Fred M Teskin
(74) *Attorney, Agent, or Firm* — Roy R. Salvagio; Robert R. Williams; Kennedy Lenart Spraggins LLP

(57) ABSTRACT

A process of forming a flame retardant material from furan dicarboxylic methyl ester (FDME) includes converting an FDME molecule to a 2,5-furan dicarbonyl dichloride (FDCC) molecule and chemically reacting the FDCC molecule with a phosphorus-containing material to form an FDME-based flame retardant material that includes a phosphorus-based flame retardant moiety.

20 Claims, 7 Drawing Sheets

(56) References Cited

U.S. PATENT DOCUMENTS

2012/0322968 A1* 12/2012 Matsuda ............... C08G 63/85
528/287
2013/0171397 A1 7/2013 Ghosh et al.
2015/0001213 A1 1/2015 Nederberg et al.
2015/0267095 A1 9/2015 Parker et al.
2016/0017089 A1 1/2016 Stephen et al.

OTHER PUBLICATIONS

AUS920160669US1, Appendix P, List of IBM Patent or Applications Treated as Related, Mar. 22, 2017, 2 pages.
Kandola et al., "Flame Retardance and Physical Properties of Novel Cured Blends of Unsaturated Polyester and Furan Resins", Polymers, Feb. 2015, vol. 7, Issue 2, pp. 298-315, Multidisciplinary Digital Publishing Institute (MDPI.com) online, DOI: doi:10.3390/polym7020298, URL: http://www.mdpi.com/2073-4360/7/2/298.
Lauzon, "Cheaper route for polyester raw material at pilot plant stage", plasticnews.com (online), Jan. 27, 2016, 2 pages, URL: http://www.plasticsnews.com/article/20160127/NEWS/160129818.

* cited by examiner

FLAME RETARDANT MATERIALS DERIVED FROM FURAN DICARBOXYLIC METHYL ESTER

BACKGROUND

Plastics are typically derived from a finite and dwindling supply of petrochemicals, resulting in price fluctuations and supply chain instability. Replacing non-renewable petroleum-based polymers with polymers derived from renewable resources may be desirable. However, there may be limited alternatives to petroleum-based polymers in certain contexts. To illustrate, particular plastics performance standards may be specified by a standards body or by a regulatory agency. In some cases, alternatives to petroleum-based polymers may be limited as a result of challenges associated with satisfying particular plastics performance standards.

SUMMARY

In a particular embodiment, a process of forming a flame retardant material from furan dicarboxylic methyl ester (FDME) is disclosed. The process includes converting an FDME molecule to a 2,5-furan dicarbonyl dichloride (FDCC) molecule. The process also includes chemically reacting the FDCC molecule with a phosphorus-containing material to form an FDME-derived flame retardant material that includes a phosphorus-based flame retardant moiety.

In another embodiment, an FDME-derived flame retardant material is disclosed. The FDME-derived flame retardant material is formed by a process that includes converting an FDME molecule to an FDCC molecule and chemically reacting the FDCC molecule with a phosphorus-containing material to form an FDME-derived flame retardant material that includes a phosphorus-based flame retardant moiety.

In yet another embodiment, an FDME-derived flame retardant material is disclosed. The FDME-derived flame retardant material is formed by a process that includes converting an FDME molecule to an FDCC molecule. The process also includes chemically reacting the FDCC molecule with a phosphorus-containing material to form a first FDME-derived flame retardant material that includes a phosphorus-based flame retardant moiety. The process further includes chemically reacting the first FDME-derived flame retardant material with an alcohol-functionalized reactive group to form a second FDME-derived flame retardant material. The second FDME-derived flame retardant material includes the phosphorus-based flame retardant moiety and a cross-linkable functional group.

The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes flame retardant (FR) materials derived from furan dicarboxylic methyl ester (FDME), also referred to herein as FDME-derived FR materials, and methods of forming FDME-derived FR materials. The FDME-derived FR materials of the present disclosure include at least one phosphorus moiety bonded to the furan moiety of the FDME starting material. Bonding the phosphorus moiety (or moieties) to the furan moiety imparts flame retardancy characteristics to the resulting FDME-derived materials. In some cases, the FDME-derived FR materials may also include one or more cross-linkable functional groups that provide matrix bonding functionality.

The FDME-derived FR materials of the present disclosure may be formed by converting an FDME molecule to a 2,5-furan dicarbonyl dichloride (FDCC) molecule and subsequently imparting flame retardancy characteristics to the FDCC molecule via addition of a phosphorus-containing material. In some cases, the FDME molecule may be synthesized from renewable resource-derived fructose. Accordingly, the FDME-derived FR materials of the present disclosure may be used to increase the renewable content in a polymeric material, while simultaneously imparting flame retardant characteristics and potentially reducing or eliminating the need for flame retardant additives.

Through the use of stoichiometric control, the FDME-derived FDCC molecule may be mono-functionalized or multi-functionalized with a phosphorus-containing flame retardant. For mono-functionalized FDCC, the molecule may be further functionalized with a matrix bonding functionality. In some cases, the FDME-derived FR materials of the present disclosure may be blended with conventional or non-conventional polymers to increase bio-content and render the polymer flame retardant.

Figure 1:
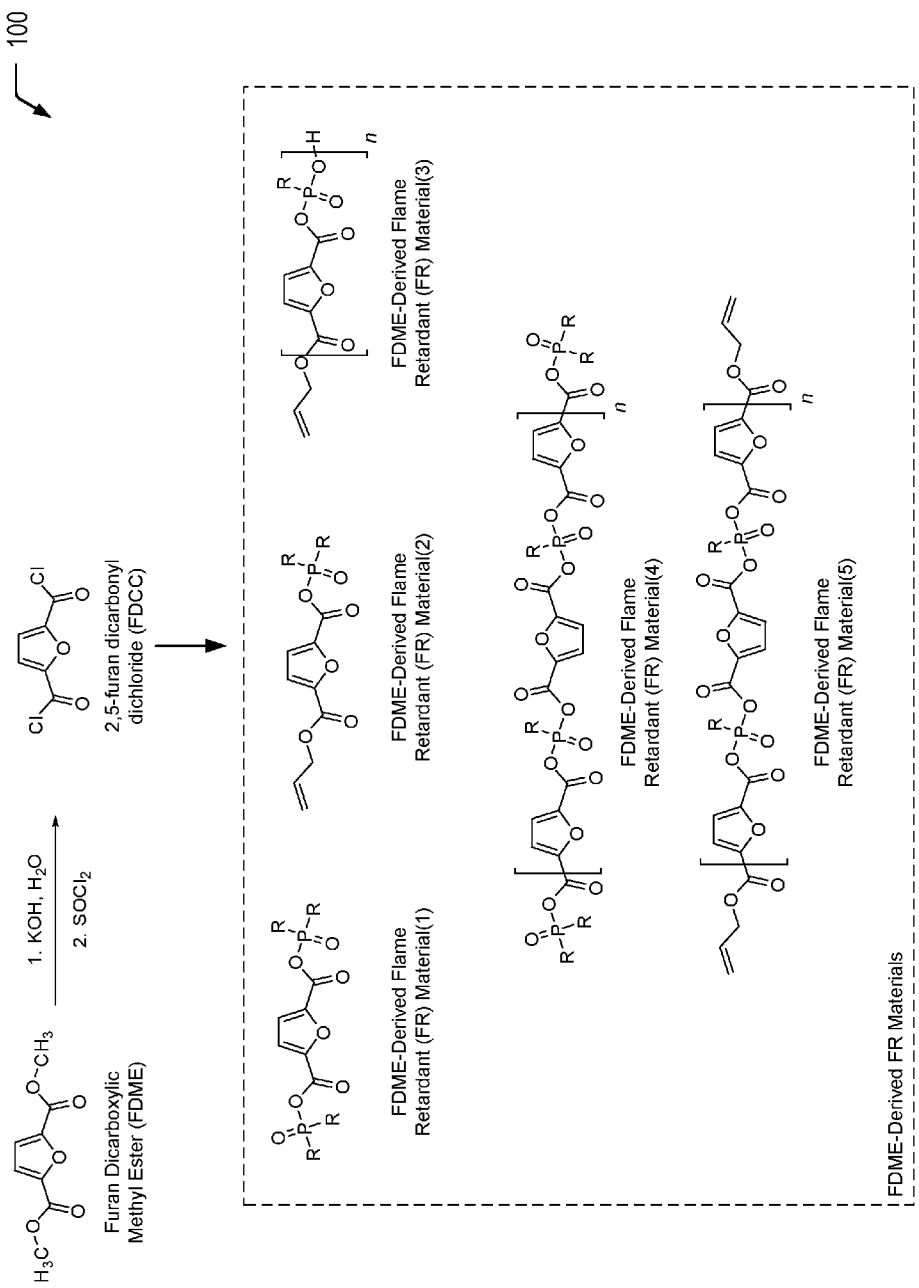
FIG. 1 is a diagram showing examples of FDME-derived flame retardant materials, according to one embodiment.

Referring to FIG. 1, a diagram 100 illustrates examples of FDME-derived FR materials according to the present disclosure. FIG. 1 illustrates that an FDME molecule may be converted to an FDCC molecule, and the FDME-derived FDCC molecule may be chemically reacted with a phosphorus-containing material to form an FDME-derived FR material. FIG. 1 illustrates five examples of FDME-derived FR materials that may be formed from the FDME-derived FDCC molecule. The example FDME-derived FR materials depicted in FIG. 1 may be formed according to the processes described herein with respect to FIGS. 2-6.

The chemical reaction depicted at the top of FIG. 1 illustrates the conversion of an FDME molecule to an FDCC molecule via saponification and subsequent thionyl chloride chlorination reactions (illustrated as steps 1 and 2 in FIG. 1). As a prophetic example, FDME may be added to an aqueous solution of KOH (3M), and stirred vigorously at 80° C. The reaction may also contain an organic solvent such as THF, and heated to reflux. Upon completion, the reaction mixture may be cooled to room temperature, and extracted with diethyl ether. The combined aqueous layers may be acidified with an aqueous acid such as 3M HCl, and extracted with diethyl ether. The solvents may be removed in vacuo and the crude product may be purified by recrystallization. Subsequently, the carboxylic acid product may be added, dropwise, to $SOCl_2$ (excess) at 0° C. The mixture may be allowed to warm up to room temperature, or heated to reflux and may be stirred for 2 hours. The solvent is removed in vacuo and the residue may be distilled to give the product.

FIG. 1 illustrates that the FDME-derived FDCC product may subsequently be utilized to form various flame retardant molecules/oligomers/polymers (collectively referred to herein as "FDME-derived FR materials") that include one or more phosphorus-based flame retardant moieties and optionally one or more cross-linkable moieties.

In some cases, the FDME-derived FDCC product may be utilized to form a first FDME-derived FR molecule that is functionalized with two flame retardant moieties (identified as "FDME-Derived FR Material(1)" in FIG. 1). The first FDME-derived FR molecule depicted in FIG. 1 represents an example of a di-functionalized, halogen-free flame retardant formed from the FDME-derived FDCC molecule. The first FDME-derived FR molecule depicted in FIG. 1 may be formed from FDME-derived FDCC according to the process illustrated and described further herein with respect to FIG. 2.

In other cases, the FDME-derived FDCC product may be utilized to form a second FDME-derived FR molecule that is functionalized with one flame retardant moiety and one cross-linkable moiety (identified as "FDME-Derived FR Material(2)" in FIG. 1). In the particular embodiment illustrated in FIG. 1, the cross-linkable moiety includes a terminal allyl group. The second FDME-derived FR molecule depicted in FIG. 1 represents an example of a mono-functionalized, halogen-free flame retardant formed from the FDME-derived FDCC molecule. In contrast to the di-functionalized halogen-free flame retardant, mono-functionalization enables a cross-linkable moiety to be bonded to the furan group. The second FDME-derived FR molecule depicted in FIG. 1 may be formed from FDME-derived FDCC according to the process illustrated and described further herein with respect to FIG. 3.

FIG. 1 further illustrates that, in some cases, the FDME-derived FDCC product may be utilized to form an FDME-derived FR oligomer (identified as "FDME-Derived FR Material(3)" in FIG. 1) that includes multiple repeat units (identified by the integer n) where each repeat unit includes a phosphorus moiety bonded to a furan moiety. The FDME-derived oligomer depicted in FIG. 1 includes a terminal cross-linkable moiety (e.g., a terminal allyl group). The FDME-derived FR oligomer depicted in FIG. 1 may be formed from FDME-derived FDCC according to the process illustrated and described further herein with respect to FIG. 4.

FIG. 1 further illustrates that the FDME-derived FDCC product may be utilized to form an FDME-derived FR polymer (identified as "FDME-Derived FR Material(4)" in FIG. 1) that includes multiple repeat units (identified by the integer n) where each repeat unit includes a phosphorus moiety bonded to a furan moiety. The FDME-derived polymer depicted in FIG. 1 includes two terminal phosphorus moieties. The FDME-derived FR polymer depicted in FIG. 1 may be formed from FDME-derived FDCC according to the process illustrated and described further herein with respect to FIG. 5.

FIG. 1 further illustrates that the FDME-derived FDCC product may be utilized to form an FDME-derived FR polymer (identified as "FDME-Derived FR Material(5)" in FIG. 1) that includes multiple repeat units (identified by the integer n) where each repeat unit includes a phosphorus moiety bonded to a furan moiety. The FDME-derived polymer depicted in FIG. 1 includes two terminal cross-linkable moieties (e.g., allyl groups). The FDME-derived FR polymer depicted in FIG. 1 may be formed from FDME-derived FDCC according to the process illustrated and described further herein with respect to FIG. 6.

Thus, FIG. 1 illustrates examples of FDME-derived FR materials that may be formed from an FDME-derived FDCC molecule. FIG. 1 illustrates that, after converting an FDME molecule to an FDCC molecule, the resulting FDCC molecule may subsequently be utilized to form various flame retardant molecules/oligomers/polymers that include one or more phosphorus-based moieties and optionally one or more cross-linkable moieties. The phosphorus group(s) imparts flame retardancy characteristics, and the optional cross-linkable group(s) provide matrix bonding functionality.

Figure 2:
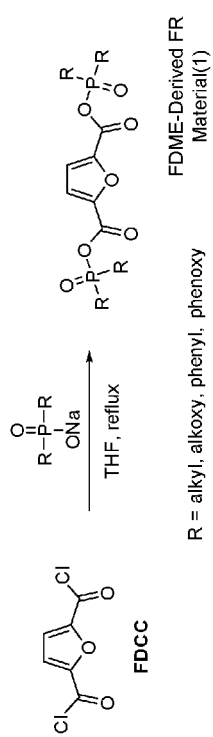
FIG. 2 is a chemical reaction diagram showing a process of forming the first FDME-derived flame retardant material depicted in FIG. 1, according to one embodiment.

Referring to FIG. 2, a chemical reaction diagram 200 illustrates an example of a process of forming the first FDME-derived FR molecule depicted in FIG. 1, according to one embodiment. FIG. 2 illustrates an example of the synthesis of a di-functionalized, halogen-free flame retardant molecule from an FDCC molecule. In a particular embodiment, the FDCC molecule of FIG. 2 may be formed from an FDME molecule according to the process described herein with respect to FIG. 1.

In FIG. 2, an FDCC molecule is reacted with sodium diphenylphosphate (R=OPh), sodium diphenylphosphonate (R=Ph), sodium dialkylphosphate (R=alkoxy), or sodium dialkylphosphonate (R=alkyl) to give the corresponding 2,5-furan dicarboxylic acid, 2,5-dianhydride with phosphate/phosphonate.

As a prophetic example, FDCC and sodium diphenylphosphate, sodium dialkylphosphate, or sodium dialkylphosphonate may be added to an organic solvent such as anhydrous THF, under an inert atmosphere (i.e., argon), and heated to reflux. Upon completion, the reaction mixture may be cooled to room temperature, and extracted with diethyl ether. The combined aqueous layers may be neutralized with an aqueous acid such as 3M HCl, and extracted with diethyl ether. The solvent may be removed in vacuo and the crude product may be purified by recrystallization, or distillation.

Figure 3:
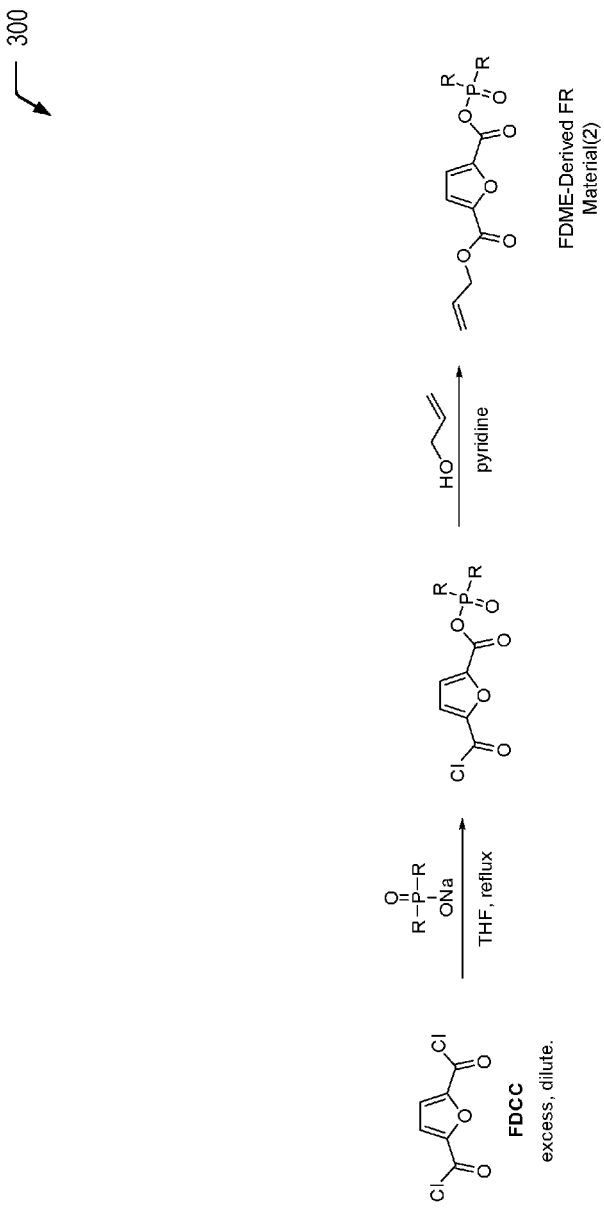
FIG. 3 is a chemical reaction diagram showing a process of forming the second FDME-derived flame retardant material depicted in FIG. 1, according to one embodiment.

Referring to FIG. 3, a chemical reaction diagram 300 illustrates an example of a process of forming the second FDME-derived FR molecule depicted in FIG. 1, according to one embodiment. FIG. 3 illustrates an example of the synthesis of a mono-functionalized, halogen-free flame retardant molecule from an FDCC molecule. In a particular embodiment, the FDCC molecule of FIG. 3 may be formed from an FDME molecule according to the process described herein with respect to FIG. 1.

FIG. 3 illustrates the synthesis of a matrix-bondable FDME-based flame retardant. An advantage associated with the FDME-based flame retardant molecule of FIG. 3 is that it allows for incorporation of a flame retardant into a polymer matrix without potentially causing detrimental properties, as the flame retardant molecule may be covalently bonded into the polymer matrix.

The first chemical reaction depicted in FIG. 3 illustrates the mono-functionalization of FDCC under dilute conditions in which an excess of FDCC is used and a sodium phosphate/phosphinate salt (where R=alkyl, alkoxy, phenyl, or phenoxy) is slowly introduced to form the monophosphorylated-FDCC molecule depicted on the right side of the chemical reaction arrow. Upon completion, the reaction mixture may be cooled to 0° C. and filtered to remove sodium chloride salt. The solvents of the filtrate may be removed in vacuo, and the crude product may be purified by recrystallization or distillation. After isolation and purification of the monophosphorylated-FDCC molecule, the second chemical reaction depicted in FIG. 3 illustrates that the remaining acid chloride group is reacted with an alcohol-functionalized reactive group (e.g., allyl alcohol) under neat reaction conditions or in an anhydrous organic solvent such as THF, with a catalytic amount of an amine such as pyridine 4-dimethylaminopyridine, or triethylamine. The reaction mixture may be heated to 60° C. or to reflux and stirred for 4 hours. The combined aqueous layers may be neutralized with an aqueous acid such as 3M HCl, and extracted with diethyl ether. The solvent may be removed in vacuo and the crude product may be purified by recrystallization, or distillation to form the second FDME-derived FR material.

While FIG. 3 illustrates an example in which the remaining acid chloride group is reacted with allyl alcohol, in other cases the remaining acid chloride group may be reacted with alternative hydroxyl-containing, multi-functional, cross-linkable moiety materials. Illustrative, non-limiting examples of other suitable reactants include glycerol 1,3-dimethacrylate; glycerol 1,3-diglycerolate diacrylate (or other multi-functional methacrylates with pendant hydroxyl groups); pent-4-ene-2-ol (or other terminal vinyl alkyl, aryl, or alkylaryl alcohol); or a 2,3-epoxy alcohol.

Figure 4:
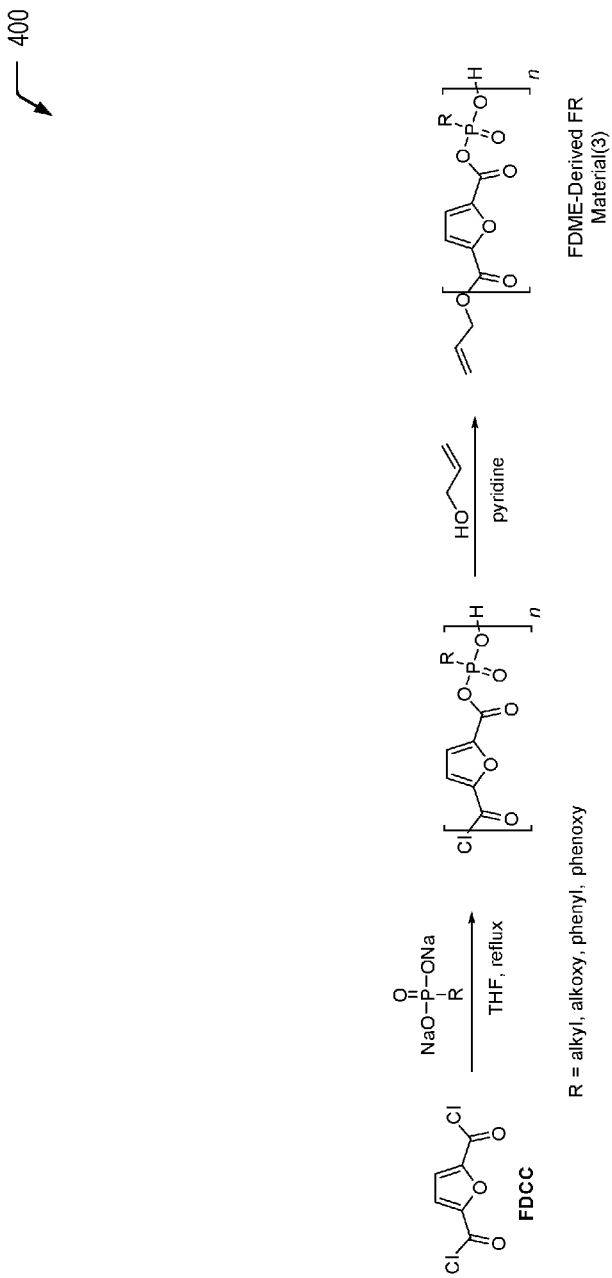
FIG. 4 is a chemical reaction diagram showing a process of forming the third FDME-derived flame retardant material depicted in FIG. 1, according to one embodiment.

Referring to FIG. 4, a chemical reaction diagram 400 illustrates an example of a process of forming the FDME-derived FR oligomer depicted in FIG. 1, according to one embodiment. In a particular embodiment, the FDCC molecule of FIG. 4 may be formed from an FDME molecule according to the process described herein with respect to FIG. 1.

The first chemical reaction of FIG. 4 illustrates the synthesis of an oligomeric (or polymeric) FDME-based FR material by reacting a 1:1 ratio of FDCC with either a phenylphosphonic acid or a phenylphosphoric acid (or sodium salt, which can be generated in situ as well) in anhydrous THF or other suitable anhydrous solvents such as dioxane or toluene, under an inert atmosphere (i.e., argon) resulting in generation of the furan-dicarboxylate-phosphate/phosphorylate polymer. The second chemical reaction of FIG. 4 illustrates that the FDME-derived FR oligomer/polymer can be terminated with a reactive functionality (e.g., allyl alcohol) to give a matrix-bondable or otherwise cross-linkable oligomer/polymer. This may occur in the same reaction vessel as the oligomer/polymer-forming step, by adding allyl alcohol or a sodium salt of allyl alcohol and stirring at reflux for an additional 4 hours, cooling to room temperature and precipitating the polymer into a solvent such as methanol, acetone, or hexane. This may occur in a separate reaction vessel after the oligomer/polymer from the first reaction step may be isolated and purified by precipitation. The polymer may be dissolve in an anhydrous solvent such as THF, dioxane, or toluene, and heated to reflux with either allyl alcohol and an amine such as pyridine, 4-dimethylaminopyridine, or triethylamine, or a sodium salt of allyl alcohol. Upon completion, cooling to room temperature and precipitating the polymer into a solvent such as methanol, acetone, or hexane.

While FIG. 4 illustrates an example in which the terminal acid chloride group is reacted with allyl alcohol, in other cases the remaining acid chloride group may be reacted with alternative hydroxyl-containing, multi-functional, cross-linkable moiety materials. Illustrative, non-limiting examples of other suitable reactants include glycerol 1,3-dimethacrylate; glycerol 1,3-diglycerolate diacrylate (or other multi-functional methacrylates with pendant hydroxyl groups); pent-4-ene-2-ol (or other terminal vinyl alkyl, aryl, or alkylaryl alcohol); or a 2,3-epoxy alcohol.

Figure 5:
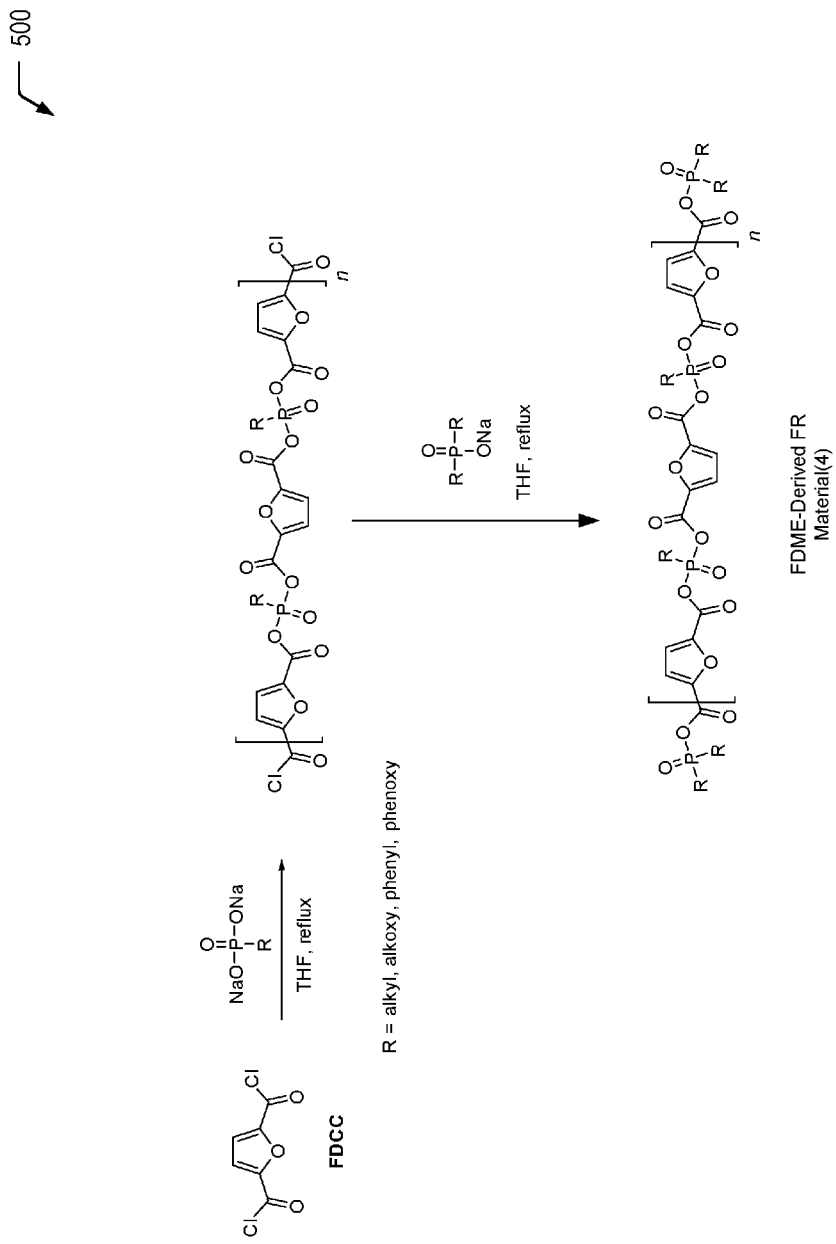
FIG. 5 is a chemical reaction diagram showing a process of forming the fourth FDME-derived flame retardant material depicted in FIG. 1, according to one embodiment.

Referring to FIG. 5, a chemical reaction diagram 500 illustrates an example of a process of forming the fourth FDME-derived FR material depicted in FIG. 1, according to one embodiment. In a particular embodiment, the FDCC molecule of FIG. 5 may be formed from an FDME molecule according to the process described herein with respect to FIG. 1.

The first chemical reaction depicted in FIG. 5 illustrates that reacting a slight excess of FDCC with either a phenylphosphonic acid or a phenylphosphoric acid (or sodium salt, which can be generated in situ as well) in anhydrous THF or other suitable anhydrous solvents such as dioxane or toluene, under an inert atmosphere (i.e., argon), and heated to reflux, results in generation of the furan-dicarboxylate-phosphate/phosphorylate oligomer/polymer depicted on the right side of the chemical reaction arrow. The second chemical reaction depicted in FIG. 5 illustrates that the use of a slight excess of FDCC results in an acid chloride terminated oligomer/polymer which can be terminated with phosphate/phosphonate groups to form the fourth FDME-derived FR material. This may occur in the same reaction vessel as the oligomer/polymer-forming step, by adding a sodium phosphate/phosphinate salt and stirring at reflux for an additional 4 hours, cooling to room temperature and precipitating the polymer into a solvent such as methanol, acetone, or hexane. This may occur in a separate reaction vessel after the oligomer/polymer from the first reaction step may be isolated and purified by precipitating the polymer into a solvent such as methanol, acetone, or hexane.

Figure 6:
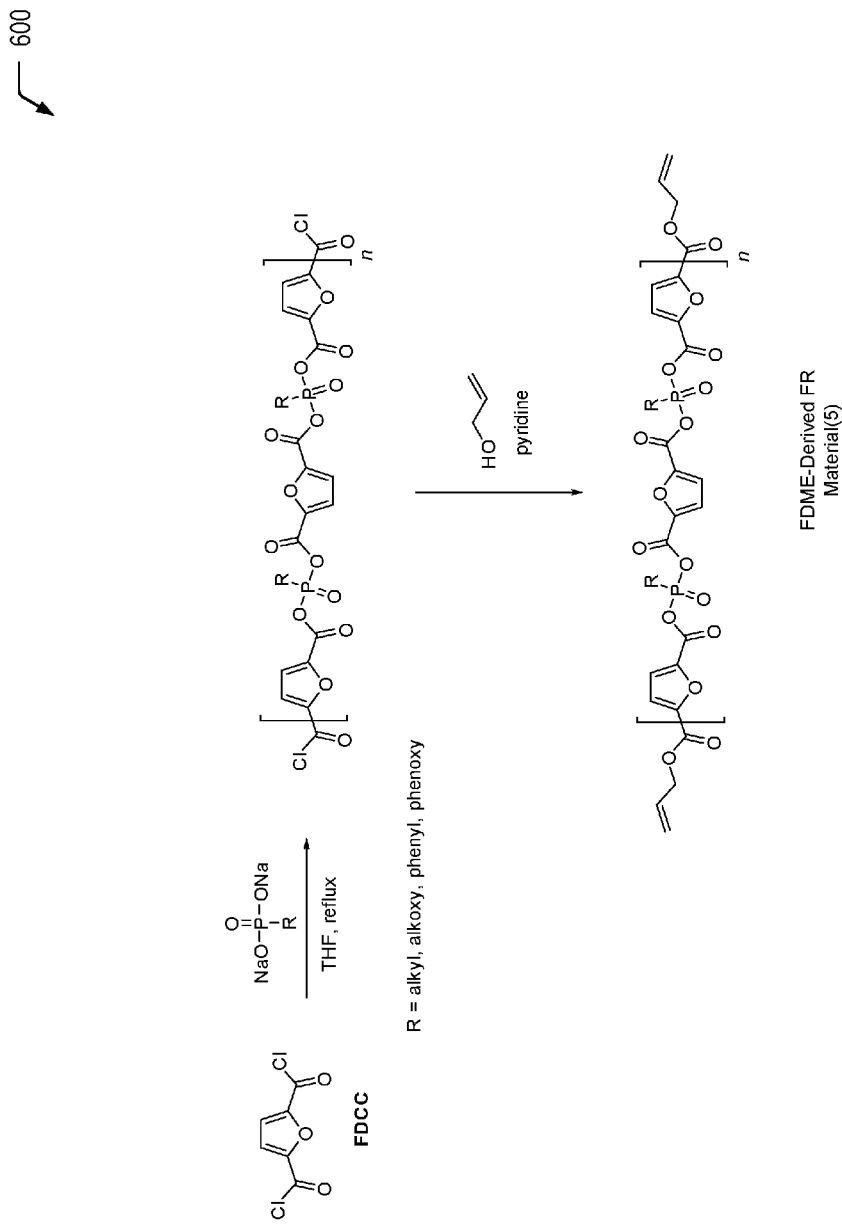
FIG. 6 is a chemical reaction diagram showing a process of forming the fifth FDME-derived flame retardant material depicted in FIG. 1, according to one embodiment.

Referring to FIG. 6, a chemical reaction diagram 600 illustrates an example of a process of forming the fifth FDME-derived FR material depicted in FIG. 1, according to one embodiment. In a particular embodiment, the FDCC molecule of FIG. 6 may be formed from an FDME molecule according to the process described herein with respect to FIG. 1.

FIG. 6 details the synthesis of oligomeric/polymeric FDME-based flame retardants, which can also be matrix-bondable. The first chemical reaction depicted in FIG. 6 illustrates that reacting a slight excess of FDCC with either a phenylphosphonic acid or a phenylphosphoric acid (or sodium salt, which can be generated in situ as well) in anhydrous TI-IF or other suitable anhydrous solvents such as dioxane or toluene, under an inert atmosphere (i.e., argon), results in generation of the furan-dicarboxylate-phosphate/phosphorylate oligomer/polymer depicted on the right side of the chemical reaction arrow. The second chemical reaction depicted in FIG. 6 illustrates that the use of a slight excess of FDCC results in an acid chloride terminated oligomer/polymer which can be reacted with an alcohol-functionalized reactive group (e.g., allyl alcohol) to form the matrix-bondable oligomer (the fifth FDME-derived FR material). This may occur in the same reaction vessel as the oligomer/polymer-forming step, by adding allyl alcohol or a sodium salt of allyl alcohol and stirring at reflux for an additional 4 hours, cooling to room temperature and precipitating the polymer into a solvent such as methanol, acetone, or hexane. This may occur in a separate reaction vessel after the oligomer/polymer from the first reaction step may be isolated and purified by precipitation. The polymer may be dissolve in an anhydrous solvent such as THF, dioxane, or toluene, and heated to reflux with either allyl alcohol and an amine such as pyridine, 4-dimethylaminopyridine, or triethylamine, or a sodium salt of allyl alcohol. Upon completion, cooling to room temperature and precipitating the polymer into a solvent such as methanol, acetone, or hexane.

While FIG. 6 illustrates an example in which the two terminal acid chloride groups are reacted with allyl alcohol, in other cases the terminal acid chloride groups may be reacted with alternative hydroxyl-containing, multi-functional, cross-linkable moiety materials. Illustrative, non-limiting examples of other suitable reactants include glycerol 1,3-dimethacrylate; glycerol 1,3-diglycerolate diacrylate (or other multi-functional methacrylates with pendant hydroxyl groups); pent-4-ene-2-ol (or other terminal vinyl alkyl, aryl, or alkylaryl alcohol); or a 2,3-epoxy alcohol.

Figure 7:
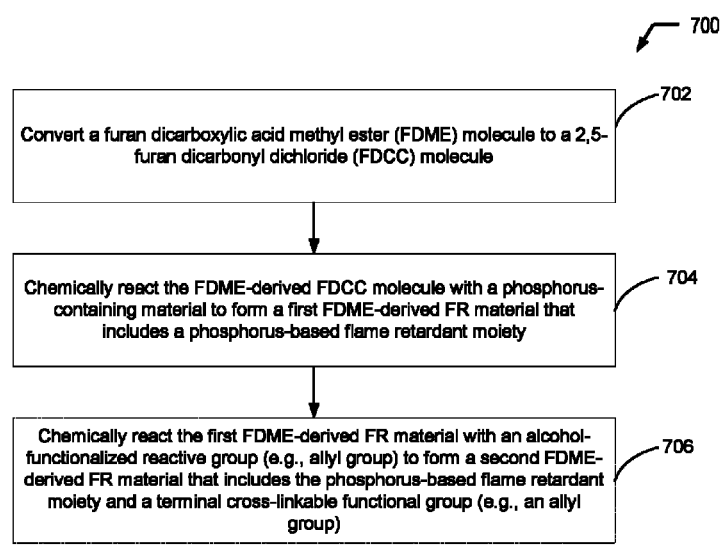
FIG. 7 is a flow diagram showing a particular embodiment of a process of forming an FDME-derived FR material.

Referring to FIG. 7, a flow diagram illustrates an example of a process 700 of forming an FDME-derived FR material. It will be appreciated that the operations shown in FIG. 7 are for illustrative purposes only and that the operations may be performed in alternative orders, at alternative times, by a single entity or by multiple entities, or a combination thereof. As an example, one entity may form FDME from renewable-resource derived fructose, while another entity may convert FDME to FDCC, while yet another entity may chemically react FDCC with a phosphorus-containing material to form an FDME-based FR material.

The process 700 includes converting an FDME molecule to an FDCC molecule, at 702. For example, referring to the chemical reaction depicted at the top of FIG. 1, an FDME molecule may be converted to an FDCC molecule via saponification and subsequent thionyl chloride chlorination reactions.

The process 700 includes chemically reacting the FDME-derived FDCC molecule with a phosphorus-containing material to form an FDME-derived FR material, at 704. For example, FIG. 1 illustrates five examples of FDME-derived FR materials that may be formed from the FDME-derived FDCC molecule. The example FDME-derived FR materials depicted in FIG. 1 may be formed according to the processes described herein with respect to FIGS. 2-6.

In the particular embodiment depicted in FIG. 7, the process 700 also includes chemically reacting the first FDME-derived flame retardant material with an alcohol-functionalized reactive group (e.g., allyl alcohol) to form a second FDME-derived flame retardant material, at 706. The second FDME-derived flame retardant material includes the phosphorus-based flame retardant moiety and a cross-linkable functional group (e.g., an allyl group). For example, referring to the first chemical reaction of FIG. 3, the intermediate material formed from the FDME-derived FDCC molecule is a molecule having a chlorocarbonyl group. The second chemical reaction of FIG. 3 illustrates the conversion of the chlorocarbonyl group to an allyl group. As another example, referring to the first chemical reaction of FIG. 4, the intermediate material formed from the FDME-derived FDCC molecule is an oligomer having a terminal chloride group. The second chemical reaction of FIG. 4 illustrates the conversion of the terminal chloride group to a terminal allyl group. As yet another example, referring to the first chemical reaction of FIG. 6, the intermediate material formed from the FDME-derived FDCC molecule is a polymer having two terminal oxychloride groups. The second chemical reaction of FIG. 6 illustrates the conversion of the terminal oxychloride groups to terminal allyl groups.

Thus, FIG. 7 illustrates an example of a process of forming an FDME-derived FR material that includes a phosphorus-based flame retardant moiety (or multiple moieties). Bonding the phosphorus moiety (or moieties) to the furan moiety imparts flame retardancy characteristics to the resulting FDME-derived materials. In some cases, the FDME-derived FR materials may also include one or more cross-linkable functional groups (e.g., allyl groups) that provide matrix bonding functionality.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a flame retardant material from furan dicarboxylic methyl ester (FDME), the process comprising:
converting a furan dicarboxylic methyl ester (FDME) molecule to a 2,5-furan dicarbonyl dichloride (FDCC) molecule; and
chemically reacting the FDCC molecule with a phosphorus-containing material to form an FDME-derived flame retardant material that includes a phosphorus-based flame retardant moiety.

2. The process of claim 1, further comprising forming the FDME molecule from renewable resource-derived fructose.

3. The process of claim 1, wherein the FDME-derived flame retardant material includes an FDME-derived flame retardant molecule that includes two phosphorus-based flame retardant moieties.

4. The process of claim 1, further comprising chemically reacting the FDME-derived flame retardant material with an alcohol-functionalized reactive group to form a second FDME-derived flame retardant material, the second FDME-derived flame retardant material including the phosphorus-based flame retardant moiety and a cross-linkable functional group.

5. The process of claim 4, wherein the alcohol-functionalized reactive group includes allyl alcohol, and wherein the cross-linkable functional group includes an allyl group.

6. The process of claim 5, wherein the second FDME-derived flame retardant material includes an FDME-derived flame retardant molecule that includes the phosphorus-based flame retardant moiety and the allyl group.

7. The process of claim 4, wherein the second FDME-derived flame retardant material includes an FDME-derived flame retardant oligomer having a terminal cross-linkable functional group and a single phosphorus-based flame retardant moiety per oligomeric repeat unit.

8. The process of claim 7, wherein the terminal cross-linkable functional group includes an allyl group.

9. The process of claim 4, wherein the second FDME-derived flame retardant material includes an FDME-derived flame retardant polymer having two terminal phosphorus-based flame retardant moieties and two phosphorus-based flame retardant moieties per polymeric repeat unit.

10. The process of claim 4, wherein the second FDME-derived flame retardant material includes an FDME-derived flame retardant polymer having two terminal cross-linkable functional groups and two phosphorus-based flame retardant moieties per polymeric repeat unit.

11. The process of claim 10, wherein the two terminal cross-linkable functional groups include allyl groups.

12. A furan dicarboxylic methyl ester (FDME)-derived flame retardant material formed by a process comprising:

converting a furan dicarboxylic methyl ester (FDME) molecule to a 2,5-furan dicarbonyl dichloride (FDCC) molecule; and chemically reacting the FDCC molecule with a phosphorus-containing material to form an FDME-derived flame retardant material that includes a phosphorus-based flame retardant moiety.

13. The FDME-derived flame retardant material of claim 12, the process further comprising forming the FDME molecule from renewable resource-derived fructose.

14. The FDME-derived flame retardant material of claim 12, wherein the FDME-derived flame retardant material includes an FDME-derived flame retardant molecule that includes two phosphorus-based flame retardant moieties.

15. A furan dicarboxylic methyl ester (FDME)-derived flame retardant material formed by a process comprising:
converting a furan dicarboxylic methyl ester (FDME) molecule to a 2,5-furan dicarbonyl dichloride (FDCC) molecule;
chemically reacting the FDCC molecule with a phosphorus-containing material to form a first FDME-derived flame retardant material that includes a phosphorus-based flame retardant moiety; and
chemically reacting the first FDME-derived flame retardant material with an alcohol-functionalized reactive group to form a second FDME-derived flame retardant material, the second FDME-derived flame retardant material including the phosphorus-based flame retardant moiety and a cross-linkable functional group.

16. The FDME-derived flame retardant material of claim 15, wherein the alcohol-functionalized reactive group includes allyl alcohol, and wherein the cross-linkable functional group includes an allyl group.

17. The FDME-derived flame retardant material of claim 16, wherein the first FDME-derived flame retardant material includes a molecule having a chlorocarbonyl group, and wherein the chlorocarbonyl group is converted to an allyl group to form the second FDME-derived flame retardant material.

18. The FDME-derived flame retardant material of claim 15, wherein the first FDME-derived flame retardant material includes an oligomer having a terminal chloride group, and wherein the terminal chloride group is converted to a terminal allyl group to form the second FDME-derived flame retardant material.

19. The FDME-derived flame retardant material of claim 16, wherein the first FDME-derived flame retardant material includes a polymer having two terminal chlorocarbonyl groups, and wherein the two terminal chlorocarbonyl groups are converted to two terminal allyl groups to form the second FDME-derived flame retardant material.

20. The FDME-derived flame retardant material of claim 19, wherein the second FDME-derived flame retardant material has two phosphorus-based flame retardant moieties per polymeric repeat unit.

* * * * *